(12) United States Patent
Navale et al.

(10) Patent No.: US 9,944,740 B2
(45) Date of Patent: Apr. 17, 2018

(54) SUGAR CONTAINING, AMPHIPHILIC COPOLYMERS

(71) Applicant: REGENTS OF THE UNIVERSITY OF MINNESOTA, Minneapolis, MN (US)

(72) Inventors: Tushar S. Navale, Mumbai (IN); Jeffrey M. Ting, Minneapolis, MN (US); Frank S. Bates, St. Cloud, MN (US); Theresa M. Reineke, Vadnais Heights, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 134 days.

(21) Appl. No.: 14/889,311

(22) PCT Filed: May 6, 2014

(86) PCT No.: PCT/US2014/036988
§ 371 (c)(1),
(2) Date: Nov. 5, 2015

(87) PCT Pub. No.: WO2014/182710
PCT Pub. Date: Nov. 13, 2014

(65) Prior Publication Data
US 2016/0120984 A1    May 5, 2016

Related U.S. Application Data

(60) Provisional application No. 61/819,923, filed on May 6, 2013.

(51) Int. Cl.
*C08F 220/28* (2006.01)
*A61K 9/16* (2006.01)
*A61K 47/32* (2006.01)

(52) U.S. Cl.
CPC .......... *C08F 220/28* (2013.01); *A61K 9/1635* (2013.01); *A61K 47/32* (2013.01); *C08F 2220/282* (2013.01); *C08F 2220/283* (2013.01); *C08F 2220/285* (2013.01)

(58) Field of Classification Search
None
See application file for complete search history.

(56) References Cited

U.S. PATENT DOCUMENTS

2008/0221047 A1* 9/2008 Yoshida .............. A61K 9/146
514/29

FOREIGN PATENT DOCUMENTS

| EP | 0735122 A2 | 10/1996 |
| EP | 0752457 A2 | 1/1997 |
| GB | WO 0040662 A1 * | 7/2000 ......... C08G 18/6225 |

OTHER PUBLICATIONS

Albertin, L., Stenzel, M., Barner-Kowollik, C., Foster, L. J. R., & Davis, T. P. (2004). Well-defined glycopolymers from RAFT polymerization: poly (methyl 6-O-methacryloyl-α-D-glucoside) and its block copolymer with 2-hydroxyethyl methacrylate. Macromolecules, 37(20), 7530-7537.*
Mahkam, M. (2009). New terpolymers as hydrogels for oral protein delivery application. Journal of drug targeting, 17(1), 29-35.*
Fleet, R., van den Dungen, E. T., & Klumperman, B. (2011). Novel glycopolymer brushes via ATRP: 1. synthesis and characterization. Macromolecular Chemistry and Physics, 212(20), 2191-2208.*
Kalra, B., Bankova, M., & Gross, R. A. (2005). Polymers from sugars: Chemoenzymatic synthesis and polymerization of vinylethylglucoside.*
The International Search Report (ISR) for PCT/US2014/036988 dated Aug. 14, 2014, pp. 1-7.
Chinese Patent Application No. 201480026063.2 Search Report dated Nov. 24, 2016, pp. 1-2.

* cited by examiner

*Primary Examiner* — Shaojia A Jiang
*Assistant Examiner* — Dale R Miller
(74) *Attorney, Agent, or Firm* — McDonnell Boehnen Hulbert & Berghoff

(57) ABSTRACT

Disclosed herein are polymers made from at least one monomer of formulae (I), (II), (III), and (IV), in combination with a monomer of formula (V) that may be used in pharmaceutical formulations. These polymers comprise a hydrocarbon backbone and are made from monomers that contain at least one carbon-carbon double bond. Methods of making these polymers are also disclosed.

18 Claims, 8 Drawing Sheets

SUGAR CONTAINING, AMPHIPHILIC COPOLYMERS

CROSS REFERENCE TO RELATED APPLICATIONS

This application claims priority from International Application No. PCT/US2014/036988, filed, filed May 6, 2014, which claims the benefit of U.S. Provisional Application No. 61/819,923 filed May 6, 2013. The disclosures of all these applications are herein incorporated by reference in their entirety.

BACKGROUND OF THE INVENTION

Many drugs have low water solubility, and as a result, low bioavailability. In an effort to increase the bioavailability of these drugs, various formulation techniques are used. One known method includes combining such drugs with a pharmaceutically acceptable water-soluble polymer, such as an esterified cellulose ether, in an organic solvent that is optionally blended with water, to form a solution, and then spray-drying the solution. Such dry formulations 1) reduce the crystallinity of the drug, thereby minimizing the activation energy necessary for its dissolution, 2) establish hydrophilic conditions around the drug molecules, and 3) result in the improved solubility and bioavailability of the drug, i.e., its in vivo absorption by an individual upon ingestion. One commonly used esterified cellulose ether is hydroxypropyl methylcellulose acetate succinate. Unfortunately, known polymers often are not ideally suited for increasing the solubility of poorly soluble drugs as they were historically designed for other applications such as coatings.

SUMMARY OF THE INVENTION

The invention provides novel polymers which are suitable for improving the solubility of drugs. The polymers of the disclosure can be manufactured to have desirable properties and targetable length scales of intermolecular associations. The polymers of the disclosure have also substantially predetermined multicomponent chemical compositions and molecular weights.

Thus, in one aspect, disclosed herein are polymers having an acrylate-derived backbone, where the polymer comprises at least two monomeric units, wherein the first monomeric unit is derived from the monomers selected from the group consisting of:

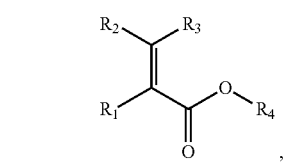

(I)

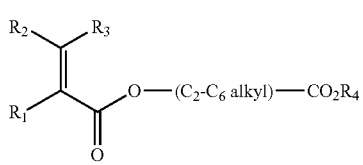

(II)

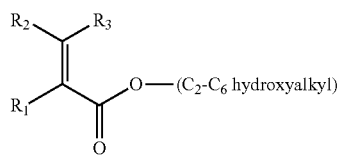

(III)

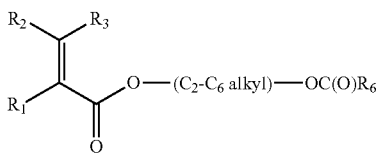

, and (IV)

and the second monomeric unit is derived from monomer of formula:

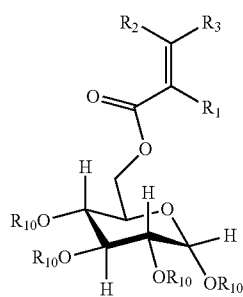

(V)

wherein at each occurrence, $R_1$, $R_2$ and $R_3$ are independently H or methyl;

$R_4$ is H or $C_1$-$C_6$ alkyl;

$R_6$ is $C_1$-$C_6$ alkyl;

at each occurrence, $R_{10}$ is independently H, $C_1$-$C_4$ alkyl, $C_2$-$C_4$ alkanoyl, $C_2$-$C_5$ alkenoyl, —$C_1$-$C_4$ alkyl-aryl, or -alkanoylaryl.

In another aspect, the disclosure provides polymers having an acrylate-derived backbone, where the polymer comprises at least two monomeric units, wherein the first monomeric unit is derived from the monomers selected from the group consisting of:

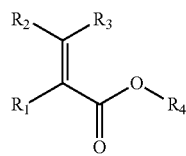

(I)

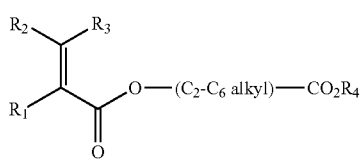

(II)

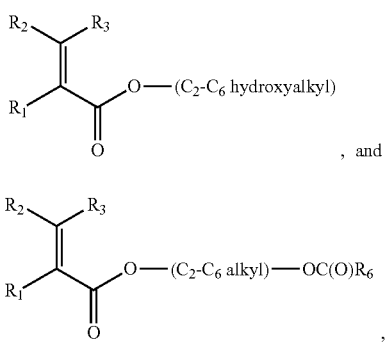

, and

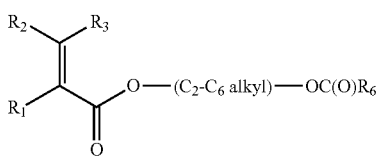

, and the second monomeric unit is derived from monomer of formula:

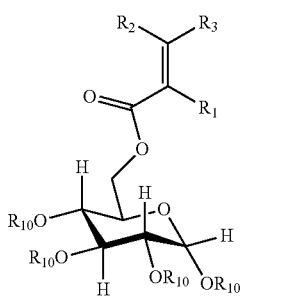

wherein at each occurrence, $R_1$, $R_2$ and $R_3$ are independently H or methyl;

$R_4$ is H or $C_1$-$C_6$ alkyl;

$R_6$ is $C_1$-$C_6$ alkyl; and at each occurrence, $R_{10}$ is independently H, $C_2$-$C_4$ alkanoyl, $C_2$-$C_5$ alkenoyl, or -alkanoylaryl;

wherein the $C_2$-$C_6$ hydroxyalkyl group has one or two OH groups.

Another aspect discloses polymers having an acrylate-derived backbone, where the polymer consists essentially of two, three, four, or five monomeric units derived from monomers selected from the group consisting of:

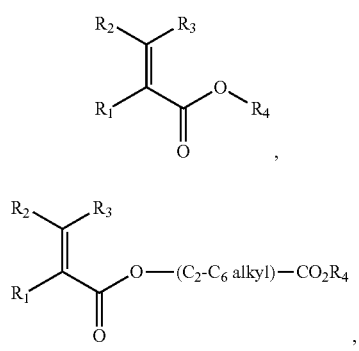

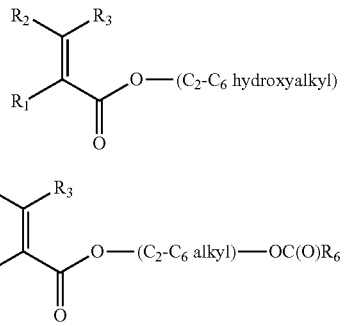

, and

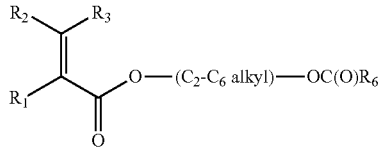

,

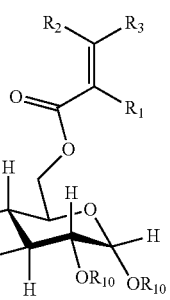

wherein at least one monomer is of formula (V) and at least one monomer is of formula (I), (II), (III), or (IV), and wherein at each occurrence, $R_1$, $R_2$ and $R_3$ are independently H or methyl;

$R_4$ is H or $C_1$-$C_6$ alkyl;

$R_6$ is $C_1$-$C_6$ alkyl; and at each occurrence, $R_{10}$ is independently H, $C_1$-$C_4$ alkyl, $C_2$-$C_4$ alkanoyl, $C_2$-$C_5$ alkenoyl, —$C_1$-$C_4$ alkyl-aryl, or -alkanoylaryl.

In another aspect, disclosed herein are pharmaceutical formulations comprising the aforementioned polymers.

In another aspect, disclosed herein are methods of making the aforementioned polymers.

DETAILED DESCRIPTION

Figure 1:
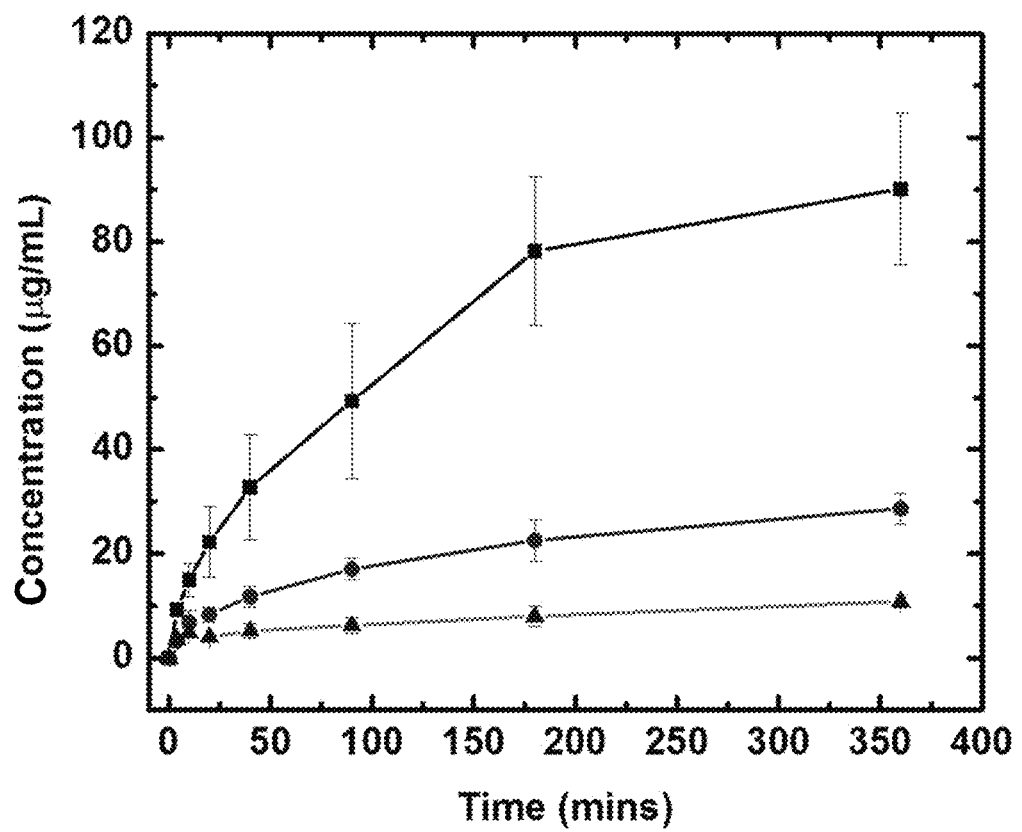
FIG. 1 is a graph of the concentration of probucol v. time, when probucol is formulated with the polymer of Sample 3.
Figure 2:
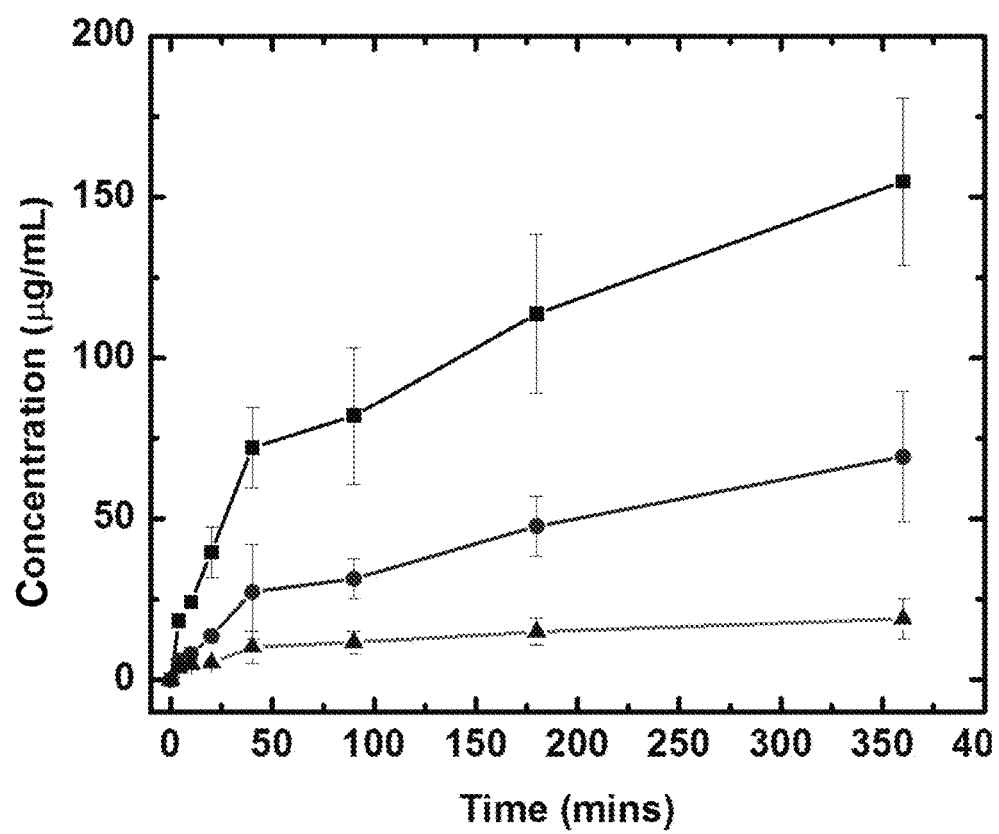
FIG. 2 is a graph of the concentration of probucol v. time, when probucol is formulated with the polymer of Sample 2.

One aspect of the disclosure provides polymers having an acrylate-derived backbone, where the polymer comprises at least two monomeric units derived from monomers that are selected from the group consisting of formula (I), (II), (III), (IV), and (V) as described above, wherein at least one monomer is of formula (V) and at least one monomer is of formula (I), (II), (III), or (IV). In one embodiment, the monomer of formula (V) is added to increase the glass transition temperature of the polymer. As one of skill would understand, the polymers of the disclosure may contain different terminal end groups depending, for example, on the initiators used and the reaction conditions.

In certain embodiments, the polymer as described above is comprised of at least about 50 mol % of monomeric units are derived from monomers of formula (I), (II), (III), (IV), and/or (V). In other embodiments, monomeric units derived from monomers selected from those of formula (I), (II), (III), (IV), and/or (V) comprise at least about 55 mol %, or at least about 60 mol %, or at least about 65 mol %, or at least about 70 mol %, or at least about 75 mol %, or at least about 80 mol %, or at least about 85 mol %, or at least about 90 mol %, or at least about 92 mol %, or at least about 95 mol %, or at least about 96 mol %, or at least about 97 mol %, or at least about 98 mol %, or at least about 99 mol % of the polymer. The remaining monomers may be selected from a variety of typical alkene monomers that undergo traditional radical polymerization, and would be apparent to those of skill in the art.

In other embodiments, the disclosure provides polymers having an acrylate-derived backbone, where the polymer consists essentially of at least two monomeric units derived from monomers that are selected from the group consisting of formula (I), (II), (III), (IV) and (V) as described above, wherein at least one monomer is of formula (V) and at least one monomer is of formula (I), (II), (III), or (IV).

In other embodiments, the disclosure provides polymers having an acrylate-derived backbone, where the polymer consists of at least two monomeric units derived from monomers that are selected from the group consisting of formula (I), (II), (III), (IV), and (V) as described above, wherein at least one monomer is of formula (V) and at least one monomer is of formula (I), (II), (III), or (IV).

In one embodiment of the above aspects, at least one occurrence of $R_1$ is H; more preferably, at least two occurrences of $R_1$ are H; and still more preferably, at least three occurrences of $R_1$ are H. In one particularly preferred embodiment, all occurrences of $R_1$ are H. In another embodiment, all occurrences of $R_1$ are methyl.

In an embodiment of the above, at least one occurrence of $R_2$ is H; more preferably, at least two occurrences of $R_2$ are H; and still more preferably, at least three occurrences of $R_2$ are H. In one particularly preferred embodiment, all occurrences of $R_2$ are H. In another embodiment, all occurrences of $R_2$ are methyl.

In another embodiment of the above, at least one occurrence of $R_3$ is H; more preferably, at least two occurrences of $R_3$ are H; and still more preferably, at least three occurrences of $R_3$ are H. In one particularly preferred embodiment, all occurrences of $R_3$ are H. In another embodiment, all occurrences of $R_3$ are methyl.

In another embodiment of the above, at least one $R_4$ is H or $C_1$-$C_6$ alkyl. Preferably, at least one $R_4$ is H or $C_1$-$C_4$ alkyl. Still more preferably, at least one $R_4$ is H. In another embodiment, all occurrences of $R_4$ are H. Alternatively, at least one $R_4$ is $C_1$-$C_4$ alkyl or more preferably, $C_1$-$C_3$ alkyl, $C_1$-$C_2$ alkyl or most preferably, methyl. In a particularly preferred embodiment, one $R_4$ is methyl, while the other is H.

In another embodiment of the above, $R_6$ is $C_1$-$C_6$ alkyl. More preferably, $R_6$ is $C_1$-$C_4$ alkyl. Still more preferably, $R_6$ is $C_1$-$C_2$ alkyl. Most preferably, $R_6$ is methyl.

In still another embodiment, $R_{10}$ is independently H, $C_1$-$C_4$ alkyl, $C_2$-$C_4$ alkanoyl, $C_2$-$C_5$ alkenyl, —$C_1$-$C_4$ alkylphenyl, or —$C_1$-$C_4$ alkanoylphenyl. More preferably, $R_{10}$ is independently H, methyl, ethyl, acetyl, acrylyl, methacrylyl, benzyl or benzoyl. Alternatively, each $R_{10}$ is H or acetyl.

In another embodiment of the above, the polymers as described above comprise of at least four monomeric units derived from monomers that are selected from the group consisting of formulas (I), (II), (III), (IV), and (V), wherein at least one monomer is of formula (V) and at least three monomers are of formula (I), (II), (III), or (IV). In one embodiment of the above, the monomer of formula (I) has the formula:

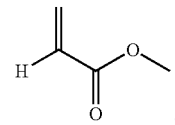

In another embodiment of the above, in the monomer of formula (II), the ($C_2$-$C_6$ alkyl) is a straight chain or branched. More preferably, the ($C_2$-$C_6$ alkyl) group is a ($C_2$-$C_4$ alkyl) group. In a preferred embodiment, the monomer of formula (II) has the formula:

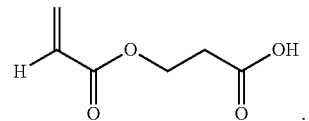

In still another embodiment of the above, in the monomer of formula (III), the ($C_2$-$C_6$ hydroxyalkyl) is straight chained or branched. More preferably, the ($C_2$-$C_6$ hydroxyalkyl) group is a ($C_2$-$C_4$ hydroxyalkyl) group. In a preferred embodiment, the monomer of formula (III) has the formula:

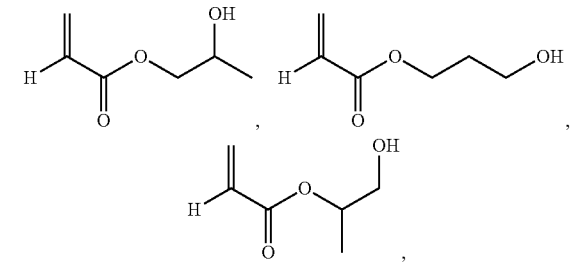

or combinations thereof.

Still more preferably, the monomer of formula (III) has the formula:

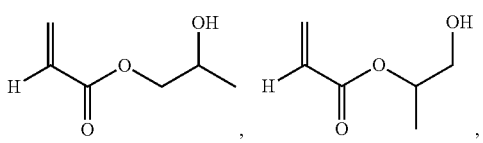

or combinations thereof.

In yet still another embodiment of the above, in the monomer of formula (IV), the ($C_2$-$C_6$ alkyl) group is a straight chain or branched. More preferably, the ($C_2$-$C_6$ alkyl) group is a ($C_2$-$C_4$ alkyl) group. In a preferred embodiment, the monomer of formula (IV) has the formula:

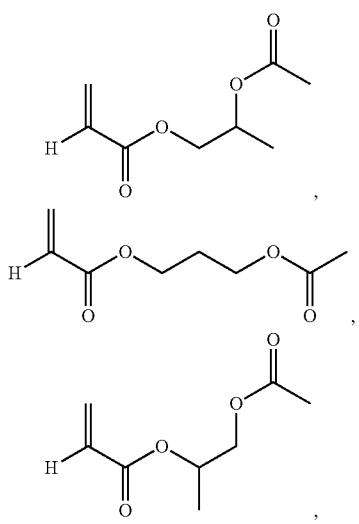

or combinations thereof.

Still more preferably, the monomer of formula (IV) has the formula:

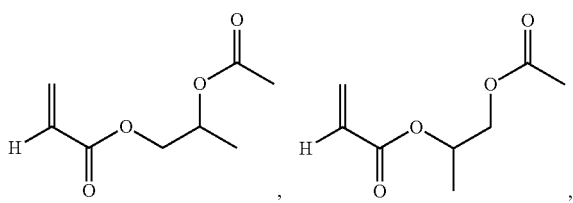

or combinations thereof.

In another embodiment of the above, the monomer of formula (V) has the formula:

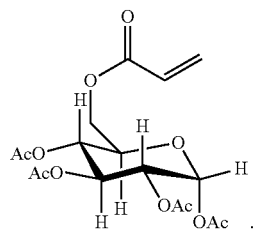

In one embodiment of the above, the polymer comprises monomeric units derived from monomers of (i.e., it was made from monomers of) formulae (I) and (V), (II) and (V), (III) and (V), or (IV) and (V). Alternatively, the polymer consists of monomeric units derived from monomers of formulae (I) and (V), (II) and (V), (III) and (V), or (IV) and (V).

In another embodiment of the above, the polymer comprises monomeric units derived from monomers of formulae (I), (II) and (V), (I), (III) and (IV), or (I), (IV) and (V). Alternatively, the polymer consists of monomeric units derived from monomers of formulae (I), (II) and (V), (I), (III) and (IV), or (I), (IV) and (V).

In still another embodiment of the above, the polymer comprises monomeric units derived from monomers of formulae (II), (III) and (V) or (II), (IV) and (V). Alternatively, the polymer consists of monomeric units derived from monomers of formulae (II), (III) and (V) or (II), (IV) and (V).

In still another embodiment of the above, the polymerized composition comprises monomers of formulae (III), (IV) and (V). Alternatively, the polymerized composition consists of monomers of formulae (III), (IV) and (V).

In yet another embodiment of the above, the polymer comprises monomeric units derived from monomers of formulae (I), (II), (III) and (V), or (I), (II), (IV) and (V), or (I), (III), (IV) and (V), or (II), (III), (IV) and (V). Alternatively, the polymer consists of monomeric units derived from monomers of formulae (I), (II), (III) and (V), or (I), (II), (IV) and (V), or (I), (III), (IV) and (V), or (II), (III), (IV) and (V).

In still yet another embodiment, the polymer comprises monomeric units derived from monomers of formulae (I), (II), (III), (IV) and (V). Alternatively, the polymer consists of monomeric units derived from monomers of formulae (I), (II), (III), (IV) and (V).

In certain embodiments, the polymers as described herein have a molecular weight within the range of from about 500 to about 500,000 g/mol. In other embodiments, the molecular weight is about 750 to about 500,000 g/mol, or about 1,000 to about 500,000, or about 10,000 to about 500,000, or about 15,000 to about 500,000, or about 20,000 to about 500,000, or about 500 to about 200,000 g/mol, or about 1,000 to about 200,000, or about 10,000 to about 200,000, or about 15,000 to about 200,000, or about 20,000 to about 200,000, or about 500 to about 100,000 g/mol, or about 1,000 to about 100,000, or about 10,000 to about 100,000, or about 15,000 to about 100,000, or about 20,000 to about 100,000, or about 1,000 to about 50,000, or about 10,000 to about 50,000, or about 15,000 to about 50,000, or about 20,000 to about 50,000, or about 10,000 to about 40,000, or about 15,000 to about 40,000, or about 20,000 to about 40,000, or less than about 500,000, or less than about 250,000, or less than about 100,000, or less than about 75,000, or less than about 70,000, or less than about 60,000, or less than about 50,000, or less than about 40,000, or less than about 30,000 g/mol. In one embodiment, the polymers as described herein have a molecular weight of about 10,000 to about 50,000 g/mol. In another embodiment, the polymers as described herein have a molecular weight of about 20,000 to about 40,000 g/mol. The person of ordinary skill in the art can, in view of the methods described herein, prepare polymers having a desired molecular weight.

The polymers produced according to this disclosure include statistical copolymers (SCPs). SCPs are long macromolecular chains consisting of two or more units whose chemical composition hinges on their constituents' relative concentrations and reactivities. SCPs typically include monomers with desirable functionalities at specific compositions to develop well-defined morphologies and physical properties. Thus, as used herein, the term "statistical polymer" or "statistical copolymer" as used herein, means a polymer that has a distribution of the monomer units along the copolymer chain that follows some statistical law, for example, Bernoullian (zero-order Markov) or first- or second-order Markov. In general, the statistical copolymers have monomeric units that have cross-reactivity ratios close to 1. Copolymers formed via Bernoullian processes have the two monomer units distributed randomly and are referred to as "random copolymers." In some embodiments, the polymers of the disclosure may be random copolymers.

It is known to those skilled in the art that monomers such as those described above can be polymerized by a variety of methods including free radical polymerization solution, emulsion polymerization, bulk polymerization, and so-called controlled radical polymerizations such as atom transfer radical polymerization, nitroxide mediated polymerization, and reversible addition-fragmentation chain transfer polymerization.

In another embodiment, the method of making the polymerized compositions comprises treating the at least three monomers, with a free radical initiator in the presence of a chain transfer agent. An example of such a method is reversible addition-fragmentation chain transfer (RAFT).

Free radical initiators are well known in the art and include azo compounds, halogens, and organic peroxides. A preferred class of initiators is the azo compounds. Examples of preferred free radical initiators include 1,1'-azobis(cyclohexanecarbonitrile) (abbreviated as ABCN); 4,4'-azobis(4-cyanopentanoic acid; and azobisisobutyronitrile (abbreviated as AIBN), with AIBN being particularly preferred.

Chain transfer agents are known in the art and include thiols, halocarbons, xanthates, dithiobenzoates, dithiocarbamates, and trithiocarbonates. Examples of chain transfer agents include bromotrichloromethane, isooctyl 3-mercaptopropionate, tert-nonyl mercaptan (mixture of isomers), pentaerythritol tetrakis(3-mercaptopropionate), 4,4'-thiobisbenzenethiol, trimethylolpropane tris(3-mercaptopropionate), Cyanomethyl methyl(phenyl)carbamodithioate, Cyanomethyl dodecyl trithiocarbonate, 2-Cyano-2-propyl benzodithioate, 4-Cyano-4-(phenylcarbonothioylthio)pentanoic acid, 2-Cyano-2-propyl dodecyl trithiocarbonate, 4-Cyano-4-[(dodecylsulfanylthiocarbonyl)sulfanyl]pentanoic acid, 2-(Dodecylthiocarbonothioylthio)-2-methylpropionic acid, and 4-cyano-4-(propylsulfanylthiocarbonyl)sulfanylpentanoic acid (CPP), which has the following formula:

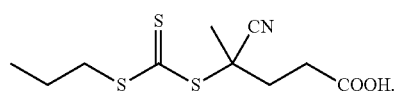 [SMILES: CCCSC(=S)SC(C)(C#N)CCC(=O)O]

One preferred chain transfer agent is CPP.

The time necessary to complete the polymerization reaction depends on the polymerization method used. Typical reaction times are from a few minutes to a week, when using RAFT.

The temperature used to complete the polymerization reaction depends on the reactants and the polymerization protocol used. Typical polymerization temperatures are from 20° C. up to the boiling point of the solvent(s)/reagents used in the reaction. Typical temperatures when using RAFT are 60-80° C., with 65-75° C. being preferred. If nitroxide mediated polymerization is used, temperatures up to 135° C. may be used.

The use of a solvent in the polymerization reactions is optional. Examples that can be used in the preparation of the claimed polymerized compositions include dimethylformamide (DMF), tetrahydrofuran (THF), toluene, xylenes, 1,4-dioxane, DMSO, methanol, ethanol, isopropanol, water, and combinations thereof.

The resulting materials may be purified using methods known in the art, such as precipitation, evaporation of volatiles to dryness, dialysis, fractionation, chromatography or trituration.

Hydrolysis reactions are known in the art and may be performed using acid or base catalysts. Suitable acid catalysts include the inorganic acids, such as HCl, $HNO_3$, $H_2SO_4$, and the organic acids, such as triflic acid, methanesulfonic acid and paratoluene sulfonic acid. Suitable bases catalysts include Group 1 and Group 2 hydroxides, such as LiOH, NaOH, and KOH, $Ca(OH)_2$. Solvents suitable for conducting the hydrolysis reaction are also known in the art. Suitable solvents include $C_1$-$C_3$ alcohols, water, dichloromethane, chloroform, and combinations of two or more thereof.

In an embodiment, the resulting polymers have the formula:

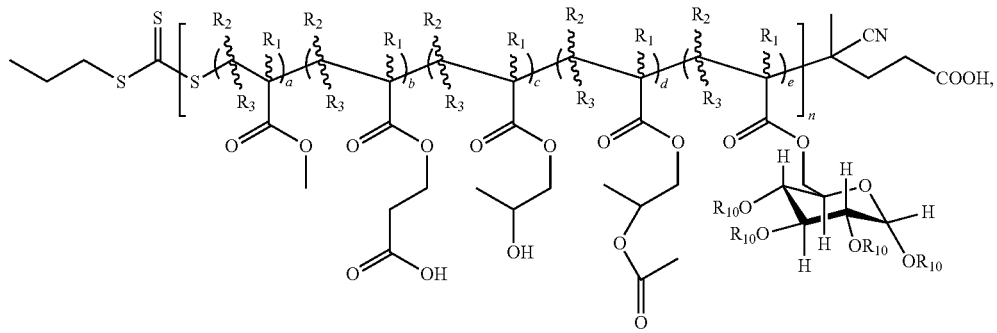

wherein $R_1$, $R_2$, $R_3$ and $R_{10}$ are as previously defined and a, b, c, and d, are 0 or an integer, e is an integer, and n is an integer. More preferably, the resulting polymers have the formula:

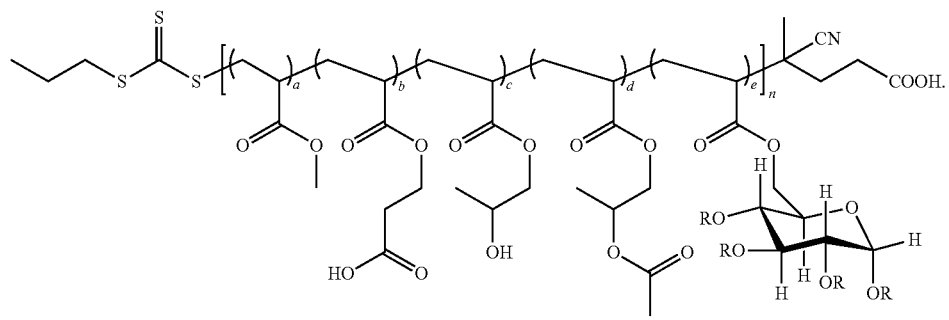

In another embodiment, disclosed herein are pharmaceutical formulations comprising the polymerized compositions described herein and at least one active pharmaceutical ingredient. Such formulations are solid dispersions that often contain hydrophobic drugs (e.g., probucol phenytoin, griseofulvin, itraconazole, ketoconazole, or danazol), wherein the formulation effectively inhibits drug crystallization in the solid-state (long-term shelf life and storage) and promotes rapid dissolution and supersaturation maintenance in the solution-state (enhanced bioavailability). While the polymerized components can be used as excipients for a vast array of drugs, the anticipated use centers on using determined relationships to optimize excipient design and formulation. This purpose can be applicable to other fields of active delivery beyond pharmaceuticals, including agriculture, coatings, food technology, personal care, and high energy materials. Other excipients, glidants, and additives may also be present in the formulations disclosed herein.

In another embodiment, disclosed herein are methods of increasing the solubility of a drug (also known as an active pharmaceutical ingredient), the methods comprising formulating the drug with the polymerized compositions disclosed herein.

Disclosed herein are racemic mixtures as well as resolved (and partially resolved) enantiomers. The resolution of enantiomers is known in the art and encompasses methods such as chiral chromatography, and fractional crystallization.

Deuterated analogs of the compounds disclosed herein are also contemplated by the instant disclosure.

Definitions

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise.

"Alkanoyl" is a group of the formula "—C(O)-alkyl."
"Alkenyl" is a group of the formula "—C(O)-alkenyl."
"Alkanoylaryl" is a group of the formula "—C(O)-alkyl-aryl."

The term "alkyl" as used herein, means a straight chain or branched hydrocarbon containing from 1 to 20 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. In some instances, the number of carbon atoms in the alkyl group is identified, e.g., $C_1$-$C_6$ alkyl. In such cases, the alkyl group has one to six carbons.

The term "alkenyl" as used herein, means a straight chain or branched hydrocarbon containing from 1 to 20 carbon atoms and also containing at least one carbon-carbon double bond, and up to two carbon-carbon double bonds. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "aryl" as used herein, means a phenyl (i.e., monocyclic aryl), or a bicyclic ring system containing at least one phenyl ring or an aromatic bicyclic ring in the aromatic bicyclic ring system, or a polycyclic ring system containing at least one phenyl ring. The rings may be fused, such as in a naphthyl group, or they may be pendant, as in biphenyl. The bicyclic aryl can be azulenyl, naphthyl, or a phenyl fused to a cycloalkyl, a cycloalkenyl, or a heterocyclyl. The bicyclic or polycyclic aryl is attached to the parent molecular moiety through any carbon atom contained within the phenyl portion of the bicyclic or polycyclic system, or any carbon atom with the napthyl, azulenyl, anthracene, or pyrene ring. More preferably, the aryl groups consist of no more than two aromatic rings. Examples of preferred aryl groups include phenyl, naphthyl, biphenyl, indene and anthracene. More preferred are phenyl and naphthyl. The most preferred aryl group is phenyl.

"Hydroxyalkyl" is an alkyl group substituted with at least one and up to three OH groups. More preferably, the hydroxyalkyl group is substituted with no more than two OH groups.

EXAMPLES

The polymers of the disclosure are illustrated further by the following examples, which are not to be construed as limiting the disclosure in scope or spirit to the specific procedures and compounds described in them.

Example 1

General RAFT Methodology

In an effort to at least partially control the RAFT polymerization process, the relative reactivities at 70° C. (in DMF)

between monomer pairs were measured to predict the feed ratio necessary for synthesizing well-defined compositions via the Walling-Briggs model. Furthermore, incorporation of the Skeist model addressed possible compositional drift, providing a simple paradigm for exerting control over macromolecular chemical architecture in a stochastic process.

The polymer length and chemical composition are tunable to simultaneously control key excipient parameters, such as hydrophobicity, hydrogen bonding, ionizability, pH response, thermal response, and degradability.

Seven free radical polymerization runs were carried out for methyl acrylate (MA) and 2-acetoxypropyl acrylate (also referred to as 2-propylacetyl acetate acrylate or PAA), with the feed monomer mole fraction ranging from 0.10 to 0.90. The AIBN concentration was kept at 1000 time less than the total monomer concentration. For instance, in run 6 the following was charged to a dried NMR tube: MA (250 μL, of 3 M solution in DMF-d$^7$, 0.75 mmol), PAA (83 μL, of 3 M solution in DMF-d$^7$, 0.25 mmol), and AIBN (10 μL, of 0.1 M solution in DMF-d$^7$, 0.001 mmol). After closing the NMR tube with rubber septum, dry nitrogen was bubbled for 15 minutes to remove dissolved oxygen. The NMR tube was then capped with a polypropylene cap and sealed with high-temperature tape under elevated nitrogen flow.

The sample was analyzed by $^1$H NMR in a Varian Inova 300 spectrometer at 22° C. to determine the initial monomer feed. The polymerization was then conducted by raising the temperature to 70° C. with the total monomer conversion kept below 15%. The total monomer conversion and molar ratio of MA to PAA in the polymer was calculated by comparing the integration of the three methoxy protons (—OCH$_3$) in MA (3.77 ppm) to corresponding methoxy protons in the copolymer (3.72 ppm), as well as the integration of the acetyl proton (—COCH$_3$) in PAA (2.01-2.06 ppm) to corresponding acetyl protons in the copolymer (2.07-2.12 ppm). A nonlinear fit $F_1=(r_{12}f_1^2+f_1f_2)/((r_{12}f_1^2+2f_1f_2+r_{21}f_2^2)$ was applied to the composition data to determine the resultant reactivity ratios $r_{MA\text{-}PAA}=0.30$, $r_{PAA\text{-}MA}=0.81$.

Example 2

Synthesis of 2-propylacetyl acrylate (PAA) by acetylation of 2-hydroxypropyl acrylate (HPA)

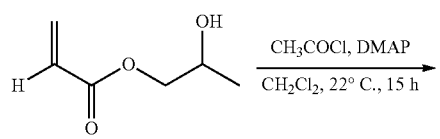

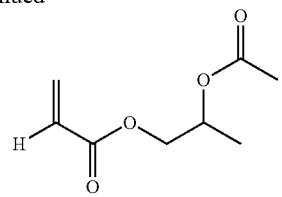

The acetylation reaction of HPA to form PAA, was conducted in 96% yield, using DMAP, and acetyl chloride in dichloromethane, using methods well known in the art. The product was a clear colorless liquid $^1$H NMR (CDCl$_3$): δ1.26 (m, 3H, —CH—CH$_3$); 2.04 (s, 3H, CO—CH$_3$); 4.02-4.26 (m, 2H, O—CH$_2$—), 5.08-5.24 (m, 1H, O-CH-CH3); 5.78-5.87 (m,1H, =C—H), 6.02-6.17 (m, 1H, =C—H); 6.34-6.44 (m, 1H, =C—H) ppm.

Note: Commercial HPA was a 2:1 mixture of the constitutional isomers 2-hydroxypropyl acrylate and 1-methyl-2-hydroxyethyl acrylate. Thus, the acetylated product was also a mixture, but the predominant isomer 2-propylacetyl acrylate is assumed for all further experiments.

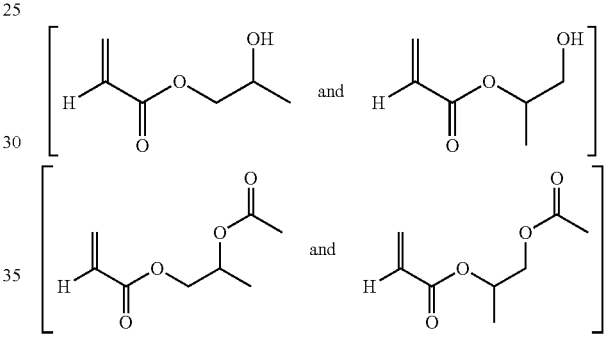

Structural isomers of hydroxypropyl acrylate and acetoxypropyl acrylate.

Example 3

Synthesis of poly(MA-stat-CEA-stat-HPA-stat-PAA-stat-GATA)

4-cyano-4-(propylsulfanylthiocarbonyl)sulfanylpentanoic acid (CPP) was synthesized according to literature procedure reported in *Macromolecules* 2008, 41, 8429-8435.

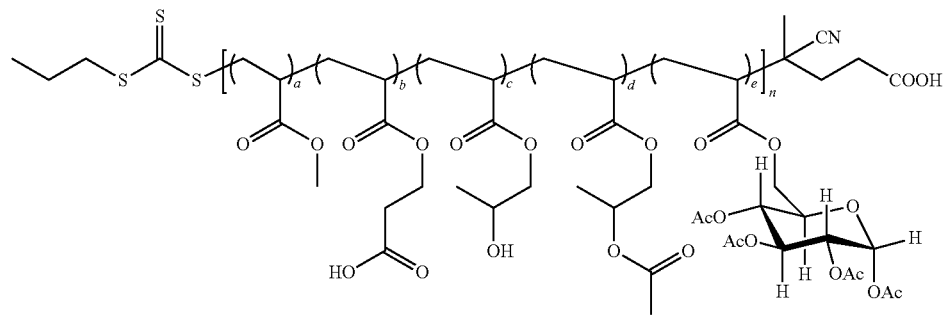

All of the following materials were received from Aldrich unless otherwise denoted. Methyl acrylate (MA), methyl methacrylate, 2-carboxyethyl acrylate (CEA), 2-carboxyethyl methacrylate, 2-hydroxypropyl acrylate (HPA), 2-hydroxypropyl methacrylate, 2-propylacetyl acrylate (PAA, synthesized in-house), 2-propylacetyl methacrylate, glucose-6-acrylate-1,2,3,4-tetraacetate (GATA, synthesized in-house), and glucose-6-methacrylate-1,2,3,4-tetraacetate were passed through a basic aluminum oxide column to remove antioxidants and inhibitors and stored at −20° C. for future use.

The copolymerization of these monomers was conducted to synthesize uniform statistical copolymers (SCPs) using reversible addition-fragmentation chain transfer (RAFT) polymerization. The initiator and chain transfer agent chosen for their compatibility with acrylates were 2,2'-azobisisobutyronitrile (AIBN) and 4-cyano-4-(propylsulfanylthiocarbonyl)sulfanylpentanoic acid (CPP, synthesized in-house). A dried 50 mL round bottom flask with measured MA, CEA, HPA, and PAA was charged AIBN and CPP in DMF. The mixture was then sealed and bubbled under nitrogen for about 25 min. After degassing, an initial sample was taken, and the reaction vessel was submerged into a preheated, well-mixed oil bath maintained at 70° C. Aliquots were taken periodically with a nitrogen-filled syringe approximately three hours by quenching to 0° C. and opening the flask to air. The resultant polymer was precipitated into diethyl ether with minimum dichloromethane. This process was repeated three times to remove excess monomers and DMF. The precipitated sample was filtered, washed, and dried under vacuum.

The following samples were made essentially according to the above described method (Table 1).

TABLE 1

| Sample # | MA | CEA | HPA | PAA | GATA | $M_n$ (Kg/mol) | Đ* |
|---|---|---|---|---|---|---|---|
| 1 | 0.53 | 0.11 | 0.15 | | 0.21 | 14.9 | 1.23 |
| 2 | 0.57 | 0.08 | 0.14 | | 0.21 | 20.6 | 1.23 |
| 3 | 0.61 | 0.05 | 0.14 | | 0.20 | 21.4 | 1.15 |
| 4 | 0.87 | 0 | 0 | 0 | 0.13 | 18.8 | 1.27 |
| 5 | | 0.83 | | | 0.17 | 20.9 | 1.23 |
| 6 | 0 | 0 | 0.83 | 0 | 0.17 | 20.4 | 1.22 |
| 7 | 0 | 0 | 0 | 0.91 | 0.09 | 19.3 | 1.29 |
| 8 | 0 | 0 | 0 | 0 | 1.00 | 16.2 | 1.41 |

*Đ is polydispersity index.

In Samples 1, 2, and 3, the values for HPA and PAA are merged, as the signals were not distinguishable by $^1$H NMR. In Samples 6 and 7, individual components were combined to make the identified, two-component polymers. $M_n$ values were measured on a SEC using THF as the eluent at 35° C. and relative to polystyrene standards.

Example 4

The Dissolution of Probucol and Phenytoin

The solubility of crystalline probucol in phosphate buffer was determined to be 4 µg/mL. Phenytoin dissolution control was determined as shown in Table 2:

TABLE 2

| Time (s) | Concentration (µg/mL) | Standard Deviation (µg/mL) |
|---|---|---|
| 0 | 0 | 0 |
| 4 | 38 | 5 |

TABLE 2-continued

| Time (s) | Concentration (µg/mL) | Standard Deviation (µg/mL) |
|---|---|---|
| 10 | 46 | 2 |
| 20 | 45 | 3 |
| 40 | 48 | 1 |
| 90 | 51 | 1 |
| 180 | 45 | 1 |
| 360 | 48 | 5 |

Example 5

Spray Drying Conditions

Spray dried dispersions were produced by spraying a 2 wt % solids solution in acetone in a mini-spray dryer (Bend Research, Inc.) at 12.8 slpm $N_2$ flow rate, 80° C. inlet temperature, and 0.65 mL/min solution flow rate. Dispersions were collected on filter paper. Drug loading was calculated based on solids, e.g. 10% phenytoin loading in the final spray dried dispersion was produced from a solution of 1.8 wt % polymer and 0.2 wt % API in acetone.

TABLE 3

| Sample # | Spray-drying Ability | $T_g$ (° C.) |
|---|---|---|
| 1 | Excellent | 69.5 |
| 2 | Excellent | 67.6 |
| 3 | Excellent | 61.5 |
| 4 | Excellent | 58.4 |
| 5 | Excellent | 35.0 |
| 6 | Excellent | 56.8, 87.7* |
| 7 | Poor | —** |

*Corresponds to the two structural isomers monomers of 2-hydroxypropyl acrylate and 1-methyl-2-hydroxyethyl acrylate.
**Homopolymer of PAA has a $T_g$ = −5.2° C.

Example 6

Synthesis of poly(glucose-6-(meth)acrylate-1,2,3,4-tetraacetate)

All of the materials were used as received from Aldrich unless otherwise denoted. To a dried 2 L round bottom flask, anhydrous glucose (60 g, 0.33 mol), trityl chloride (98 g, 0.35 mol), and anhydrous pyridine (252 mL, 3.13 mol) was added sequentially. The mixture was placed in a preheated, well-mixed oil bath at 90° C. for 15 min. When the glucose was fully dissolved, acetic acid (252 mL, 4.40 mol) was added in one portion and allowed to stir at room temperature for 12 h. Afterward, the solution was carefully poured into a mixture of ice water (10 L) and acetic acid (500 mL). The precipitated mixture was mechanically stirred for about 2 h. The resultant white precipitate was filtered, washed with cold water, and dried under ambient conditions. A simple precipitation using diethyl ether afforded pure6-trityl-β-d-glucose-1,2,3,4-tetraacetate (TGTA, 44% yield). Next, TGTA (50 g, 0.08 mol) and acetic acid (217 mL, 3.79 mol) was added to a 500 mL round bottom flask and heated at 90° C. in a oil bath under constant stirring for 15 min. When the solid fully dissolved, the reaction vessel was immersed in a salt-ice bath (about −5° C.) before carefully adding hydrogen bromide (19.56 mL, 0.80 mol) in a drop-wise manner. The reaction was stirred at the same temperature for 1 min. The resultant trityl bromide was filtered out and washed with acetic acid (4×50 mL) into cold water (1 L). The resultant mixture was extracted with dichloromethane (3×200 mL), and the collected organic layer was washed with water (3×300 mL), brine (300 mL), dried over MgSO$_4$, and evaporated under vacuum. About 100 mL of anhydrous ether was added to the viscous solution and agitated with a glass rod to effect crystallization. The solid obtained was filtered to afford β-d-glucose-1,2,3,4-tetraacetate (GTA, 88% yield) as a white solid. The product was stored at room temperature and verified with $^1$H NMR. Lastly, GTA (10 g, 0.03 mol) and triethylamine (8.66 g, 0.09 mol) was added to a stirring 500 mL round bottom flask containing acryloyl chloride (7.24 g, 0.08 mol) and THF (250 mL) under nitrogen at −5° C. for 24 h. The reaction was monitored by $^1$H NMR, and after complete consumption of GTA, the reaction mixture was diluted with water (300 mL). The resultant mixture was extracted with dichloromethane (3×200 mL), and the collected organic layer was washed with water (3×300 mL), brine (300 mL), dried over MgSO$_4$, and evaporated under vacuum to yield GATA (97% yield).

Example 7

General Procedure for Dissolution Studies Using Probucol and Phenytoin

Samples (either spray dried dispersions or crystalline API as received) were weighed into 2.0 mL conical microcentrifuge tubes in duplicate. Phosphate buffer solution (82 mM sodium chloride, 20 mM sodium phosphate dibasic, 47 mM potassium phosphate monobasic, 0.5 wt % simulated intestinal fluid powder, pH 6.5) at 37° C. was added in an amount that would produce a final concentration of drug of 1000 mg/L if all material was fully dissolved (e.g., 7.2 mg of spray dried dispersion consisting of 1.8 mg griseofulvin and 5.4 mg polymer was diluted with 1.8 mL buffer solution). Samples were vortexed 1 min and set in an isothermal aluminum sample holder set at 37° C. At each time point, samples were centrifuged 1 min at >13,000×g (g=gravitational force on earth), and a 50 μl aliquot was removed and diluted with 250 μl methanol. The samples were again vortexed 30 s and held at 37° C. until the next time point. Drug concentration in each aliquot was determined by reverse phase HPLC.

Example 8

Probucol Spray Dried Dispersions (SDDs): mDSC Results

The data below shows the claimed polymers decrease the crystallinity of the probucol in spray dried dispersions. The lower the value, the less crystalline the probucol is, and the more amorphous it is, which increases the solubility of the probucol.

TABLE 4

| Sample # | Probucol Loading | | |
|---|---|---|---|
| | 10% | 25% | 50% |
| 1 | 6 | 19 | 83 |
| 2 | 3 | 33 | 87 |
| 3 | 14 | 17 | 72 |
| 4 | 0 | 14 | 50 |
| 5 | 9 | 13 | 64 |
| 6 | 13 | 10 | 88 |
| 7 | a | a | a |
| 8 | 0 | 24 | 66 | a = low T$_g$ polymer, which could not be spray dried.

Example 9

Dissolution Data

Probucol and phenytoin concentrations were quantified using a Agilent 1260 Infinity Quaternary HPLC equipped. The HPLC consisted of a reversed-phase EC-C18 column (Poroshell 120, 4.6×50 mm, 2.7 μm, Agilent, USA). The mobile phase was acetonitrile: water 96:4 for probucol and acetonitrile: water 40:60 for phenytoin, and the flow rate was 1.0 mL/min. A 10 μL aliquot of sample was injected, and the column effluent was detected at 241 nm for probucol (eluted at 2.90 min) and 225 nm for phenytoin (eluted at 1.40 min) with a UV detector (1260 Infinity Multiple Wavelength Detector, Agilent). Tables 5-15 illustrate dissolution performance results. The standard curve linearity was verified from 0.1 to 1000 μg/mL with an $r^2$ value of at least 0.999.

TABLE 5

Sample 1 with phenytoin dissolution performance.

| Time | 10 wt % loading | | 25 wt % loading | | 50 wt % loading | |
|---|---|---|---|---|---|---|
| (s) | Value | Uncertainty | Value | Uncertainty | Value | Uncertainty |
| 0 | 0 | 0 | 0 | 0 | 0 | 0 |
| 4 | 231 | 7 | 98 | 15 | 47 | 7 |
| 10 | 218 | 2 | 103 | 15 | 49 | 6 |
| 20 | 201 | 10 | 105 | 17 | 54 | 7 |
| 40 | 177 | 14 | 106 | 15 | 60 | 6 |
| 90 | 159 | 20 | 107 | 13 | 68 | 11 |
| 180 | 188 | 32 | 128 | 9 | 86 | 5 |
| 360 | 250 | 3 | 134 | 23 | 83 | 3 |

TABLE 6

Sample 2 with phenytoin dissolution performance.

| Time | 10 wt % loading | | 25 wt % loading | | 50 wt % loading | |
|---|---|---|---|---|---|---|
| (s) | Value | Uncertainty | Value | Uncertainty | Value | Uncertainty |
| 0 | 0 | 0 | 0 | 0 | 0 | 0 |
| 4 | 89 | 18 | 70 | 2 | 40 | 3 |
| 10 | 72 | 13 | 66 | 7 | 38 | 10 |
| 20 | 66 | 17 | 60 | 6 | 43 | 8 |
| 40 | 65 | 19 | 62 | 12 | 50 | 8 |
| 90 | 61 | 18 | 56 | 6 | 51 | 3 |
| 180 | 63 | 21 | 56 | 6 | 50 | 6 |
| 360 | 57 | 9 | 54 | 5 | 57 | 1 |

TABLE 7

Sample 3 with phenytoin dissolution performance.

| Time | 10 wt % loading | | 25 wt % loading | | 50 wt % loading | |
|---|---|---|---|---|---|---|
| (s) | Value | Uncertainty | Value | Uncertainty | Value | Uncertainty |
| 0 | 0 | 0 | 0 | 0 | 0 | 0 |
| 4 | 76 | 5 | 52 | 2 | 30 | 2 |
| 10 | 63 | 5 | 58 | 2 | 41 | 4 |
| 20 | 56 | 1 | 50 | 3 | 48 | 1 |
| 40 | 48 | 1 | 45 | 1 | 43 | 7 |
| 90 | 43 | 2 | 44 | 2 | 48 | 9 |
| 180 | 54 | 3 | 42 | 2 | 47 | 6 |
| 360 | 47 | 2 | 43 | 3 | 55 | 3 |

TABLE 8

Sample 4 with probucol dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 3 | 0 | 0 | 0 | 6 | 1 |
| 10 | 3 | 0 | 1 | 0 | 9 | 8 |
| 20 | 4 | 0 | 1 | 0 | 8 | 6 |
| 40 | 7 | 1 | 1 | 0 | 6 | 3 |
| 90 | 12 | 0 | 1 | 0 | 6 | 5 |
| 180 | 19 | 1 | 1 | 0 | 9 | 5 |
| 360 | 29 | 1 | 3 | 0 | 14 | 10 |

TABLE 9

Sample 4 with phenytoin dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 53 | 8 | 32 | 4 | 19 | 2 |
| 10 | 58 | 8 | 34 | 4 | 25 | 2 |
| 20 | 65 | 11 | 41 | 5 | 31 | 0 |
| 40 | 67 | 11 | 46 | 4 | 37 | 2 |
| 90 | 71 | 6 | 47 | 3 | 41 | 1 |
| 180 | 65 | 14 | 47 | 2 | 43 | 2 |
| 360 | 64 | 16 | 47 | 2 | 45 | 1 |

TABLE 10

Sample 5 with probucol dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 829 | 0 | 521 | 6 | 96 | 3 |
| 10 | 823 | 2 | 501 | 23 | 101 | 9 |
| 20 | 900 | 42 | 576 | 5 | 145 | 32 |
| 40 | 868 | 14 | 557 | 4 | 123 | 18 |
| 90 | 903 | 2 | 544 | 1 | 125 | 25 |
| 180 | 908 | 43 | 583 | 23 | 128 | 31 |
| 360 | 881 | 62 | 558 | 107 | 143 | 23 |

TABLE 11

Sample 5 with phenytoin dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 109 | 1 | 69 | 1 | 58 | 1 |
| 10 | 95 | 1 | 69 | 2 | 54 | 0 |
| 20 | 91 | 0 | 70 | 4 | 56 | 0 |
| 40 | 85 | 2 | 66 | 0 | 58 | 1 |
| 90 | 77 | 3 | 63 | 1 | 56 | 5 |
| 180 | 72 | 1 | 58 | 1 | 50 | 4 |
| 360 | 72 | 0 | 54 | 1 | 47 | 2 |

TABLE 12

Sample 6 with probucol dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 5 | 1 | 2 | 0 | 4 | 1 |
| 10 | 5 | 1 | 2 | 0 | 4 | 0 |
| 20 | 5 | 1 | 3 | 0 | 5 | 1 |
| 40 | 5 | 1 | 4 | 0 | 7 | 1 |
| 90 | 6 | 1 | 4 | 0 | 11 | 0 |
| 180 | 6 | 1 | 5 | 1 | 11 | 0 |
| 360 | 7 | 1 | 5 | 1 | 9 | 0 |

TABLE 13

Sample 6 with phenytoin dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 50 | 7 | 26 | 5 | 23 | 1 |
| 10 | 60 | 9 | 32 | 9 | 35 | 1 |
| 20 | 61 | 5 | 36 | 8 | 36 | 5 |
| 40 | 71 | 5 | 41 | 2 | 41 | 5 |
| 90 | 71 | 1 | 42 | 3 | 46 | 2 |
| 180 | 69 | 7 | 48 | 0 | 52 | 1 |
| 360 | 79 | 6 | 49 | 1 | 47 | 5 |

TABLE 14

Sample 8 with probucol dissolution performance

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | — | 0 | — | 0 | — |
| 4 | 15 | — | 9 | — | 3 | — |
| 10 | 23 | — | 9 | — | 8 | — |
| 20 | 31 | — | 13 | — | 8 | — |
| 40 | 39 | — | 17 | — | 4 | — |
| 90 | 46 | — | 25 | — | 4 | — |
| 180 | 50 | — | 27 | — | 6 | — |
| 360 | 55 | — | 32 | — | 9 | — |

TABLE 15

Sample 8 with phenytoin dissolution performance.

| Time (s) | 10 wt % loading | | 25 wt % loading | | 50 wt % loading | |
|---|---|---|---|---|---|---|
| | Value | Uncertainty | Value | Uncertainty | Value | Uncertainty |
| 0 | 0 | 0 | 0 | 0 | 0 | 0 |
| 4 | 80 | 3 | 68 | 1 | 56 | 2 |
| 10 | 81 | 12 | 64 | 1 | 49 | 6 |
| 20 | 70 | 4 | 72 | 12 | 56 | 7 |
| 40 | 71 | 5 | 66 | 9 | 56 | 6 |
| 90 | 63 | 3 | 64 | 6 | 54 | 3 |
| 180 | 57 | 1 | 59 | 2 | 54 | 1 |
| 360 | 53 | 3 | 53 | 2 | 51 | 5 |

All 5-component polymers were soluble acetone, dichloromethane, THF, DMF, DMSO, dioxane at room temperature. Sample 1 (see Table 1) was soluble in pH 6.5 aqueous buffer, while samples 2 and 3 (see Table 1) were insoluble in pH 6.5 aqueous buffer.

Example 10

Acetate Removal

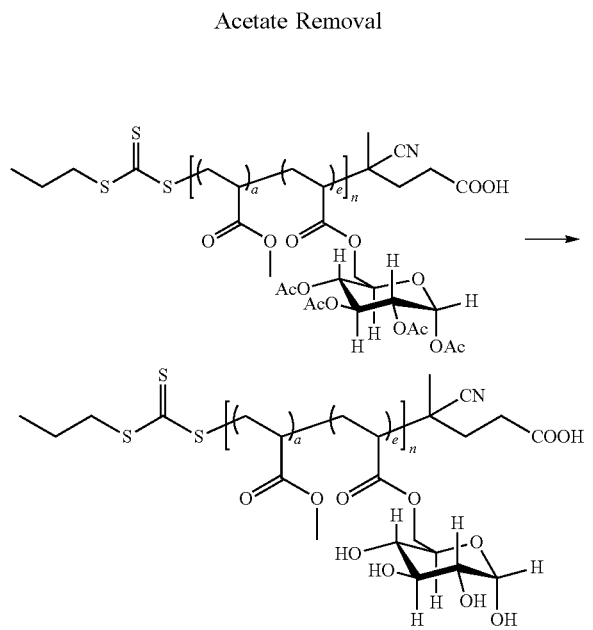

Figure 3A:
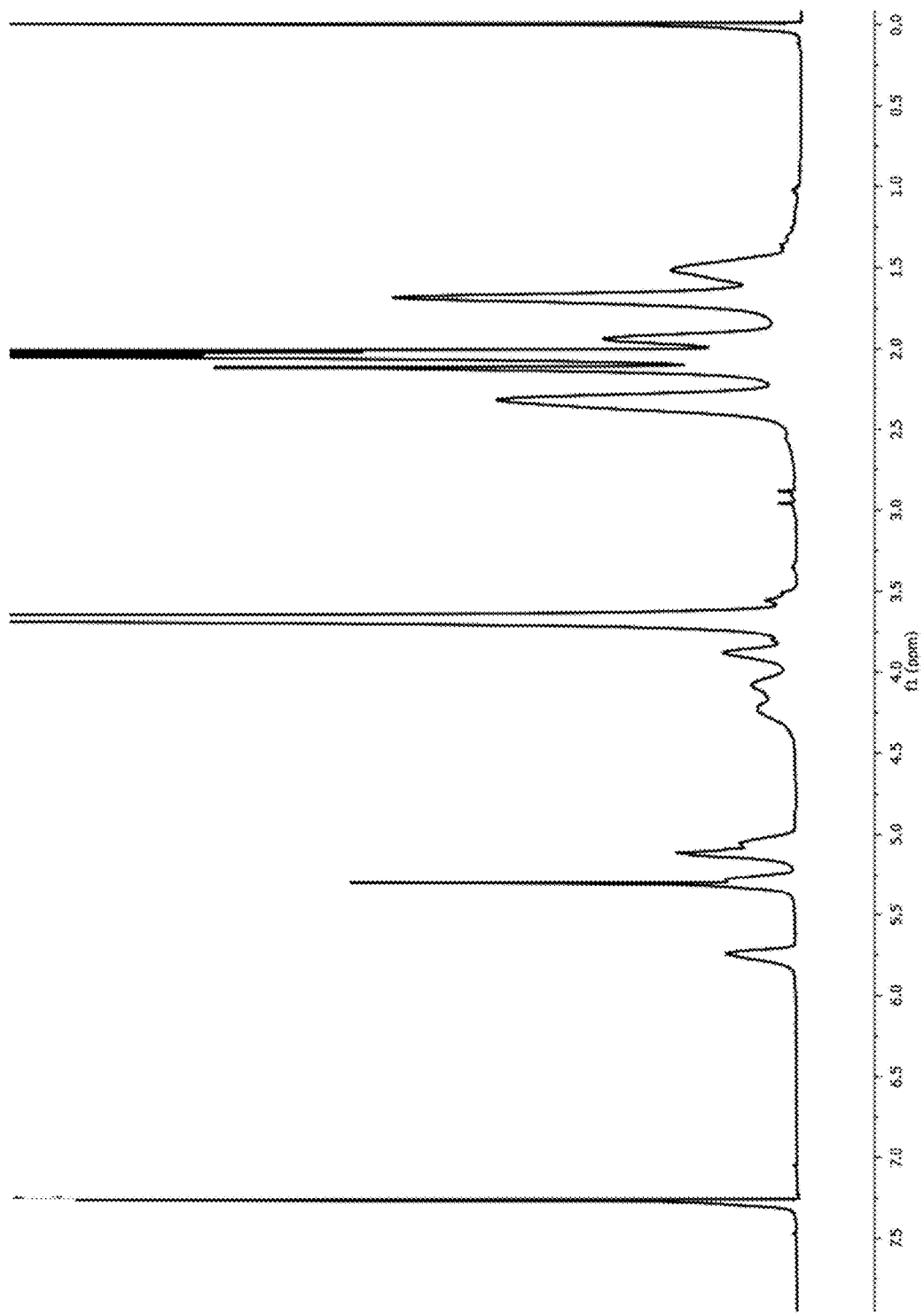
FIG. 3A shows a 300 MHz $^1$H NMR spectrum of the starting material for Example 10.
Figure 3B:
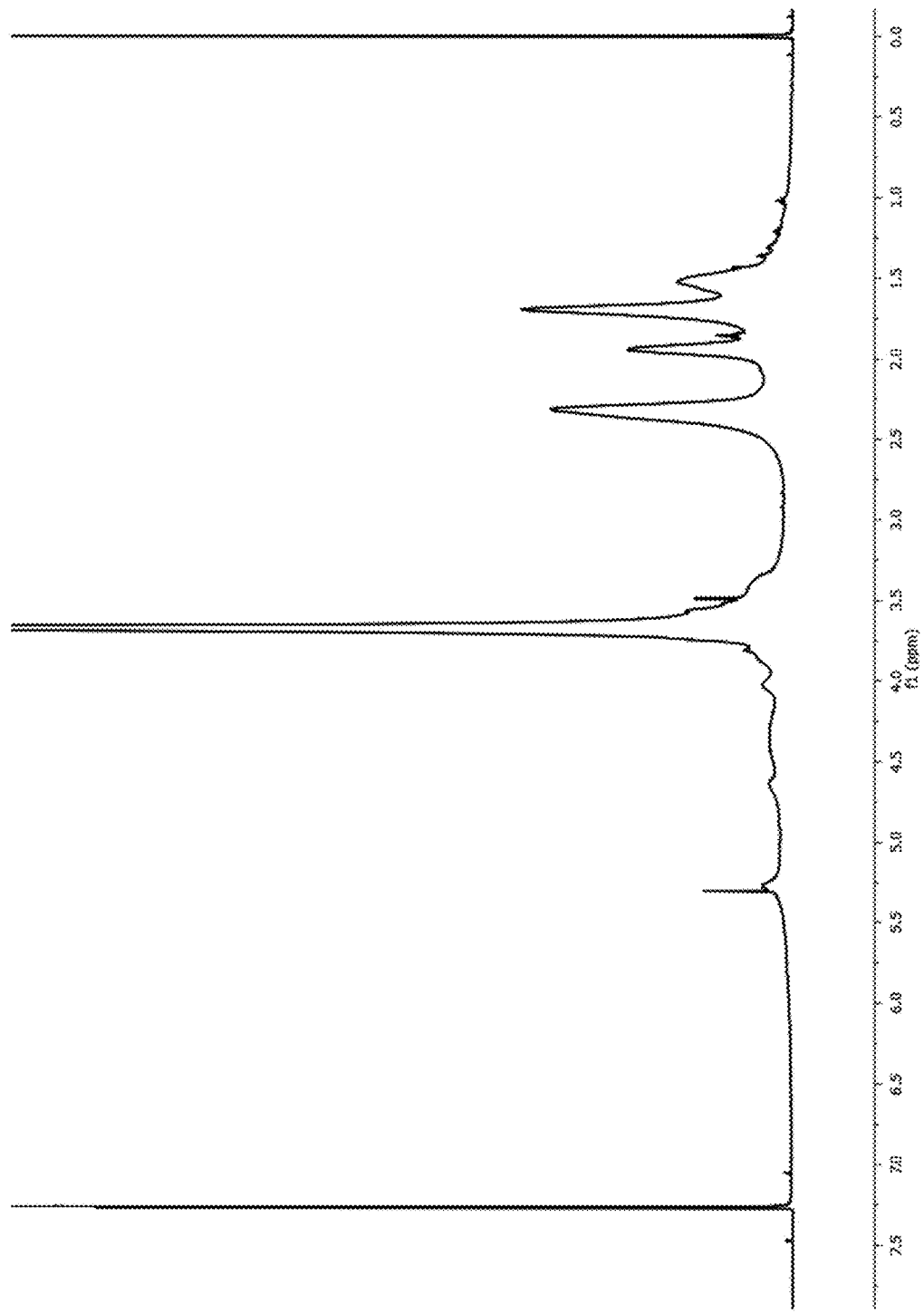
FIG. 3B shows a 300 MHz $^1$H NMR spectrum of the product for Example 10.

The above reaction was successfully performed using NaOMe in CHCl$_3$/MeOH (1:1) at 22° C. A $^1$H NMR spectrum of the starting material may be seen in FIG. 3A, while a $^1$H NMR spectrum of the product may be seen in FIG. 3B.

Example 11

Acetate Removal

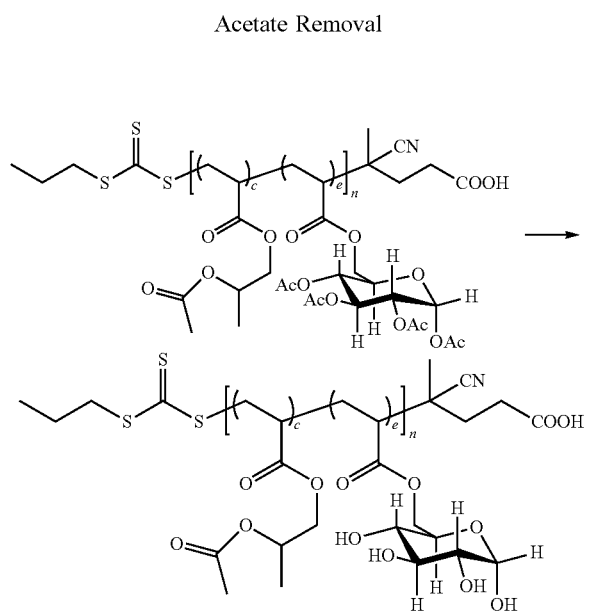

Figure 4:
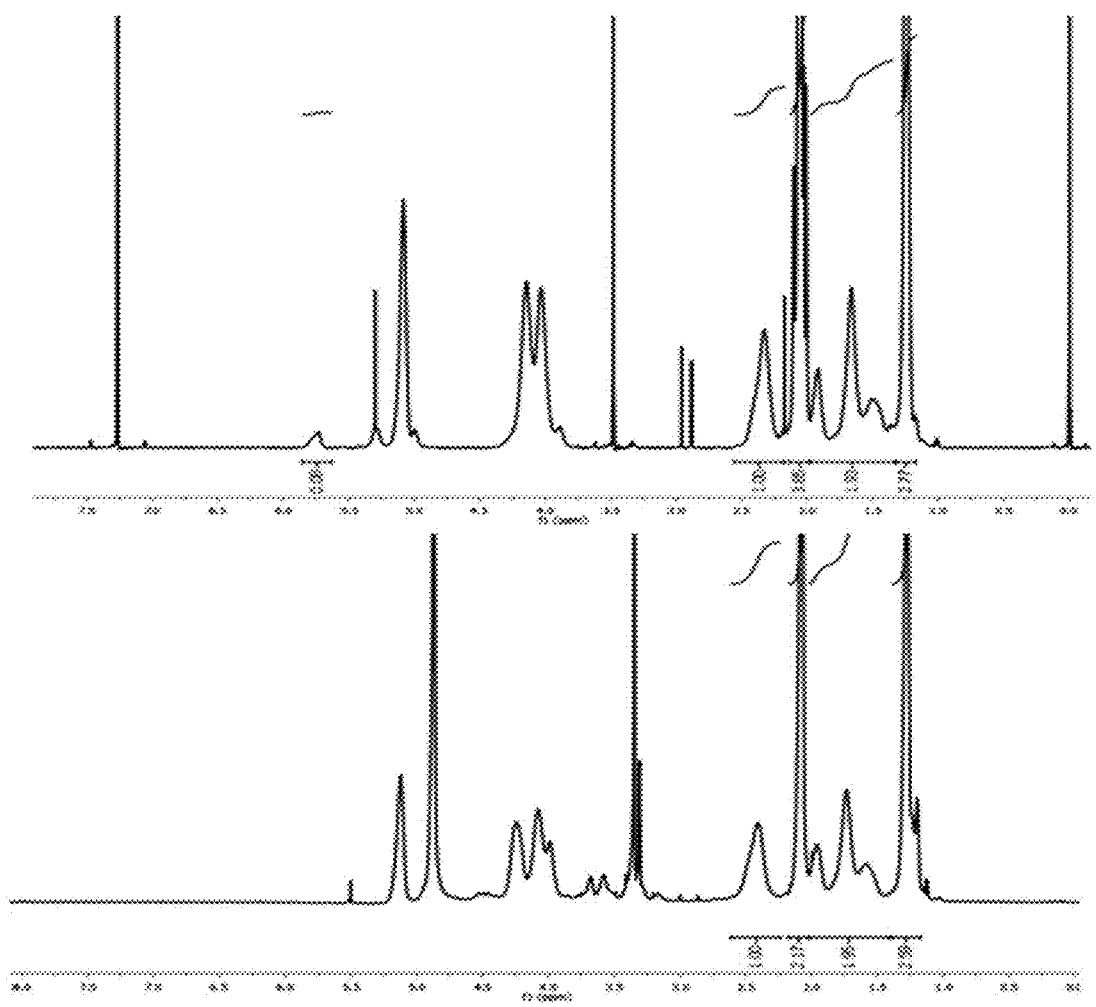
FIG. 4 shows two $^1$H NMR spectra: top spectrum is of the starting material for Example 11, and the bottom spectrum is of the product for Example 11.

The above reaction was successfully performed using NaOMe in CHCl$_3$/MeOH (1:1) at 22° C. A $^1$H NMR spectrum of the starting material may be seen in FIG. 4 (top spectrum), while a $^1$H NMR spectrum of the product may also be seen in FIG. 4 (bottom spectrum).

Example 12

Acetate Removal

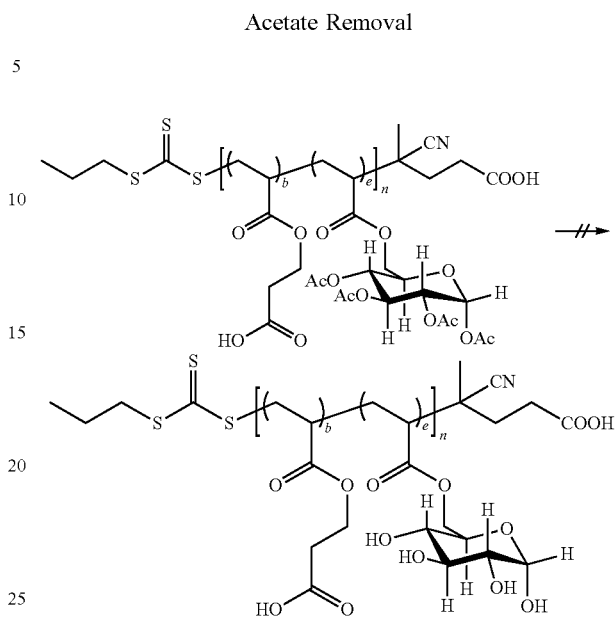

Figure 5A:
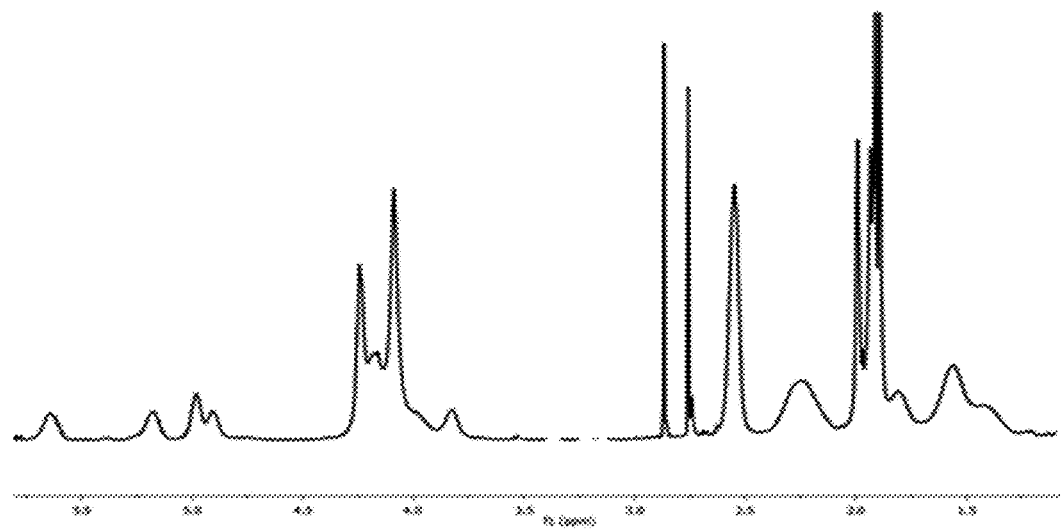
FIG. 5A shows a portion of a 300 MHz $^1$H NMR spectrum for the acetate protected starting material of Example 12.
Figure 5B:
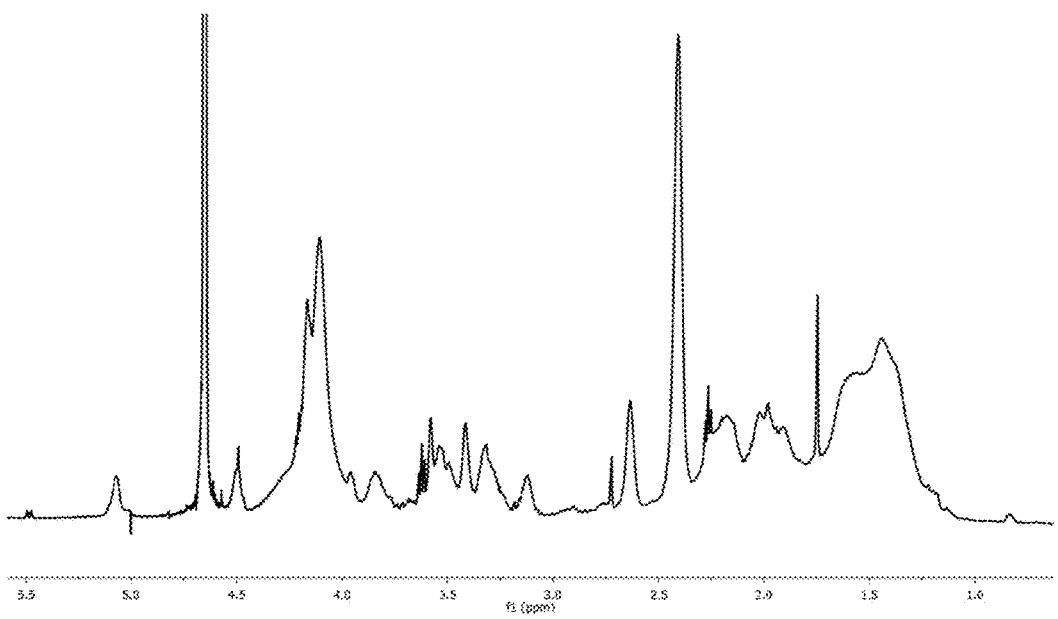
FIG. 5B shows a portion of a 300 MHz $^1$H NMR spectrum for the deprotected product of Example 12.

The use of NaOMe in CHCl$_3$/MeOH (1:1) at 22° C. resulted in over deprotection. FIG. 5A is a $^1$H NMR of the starting material, while FIG. 5B is a $^1$H NMR of the deprotected product. Note the absence of the acetate methyl groups from approximately 2 ppm in the product, which shows that the starting material was successfully deprotected.

Example 13

Acetate Removal from a Two Component Polymer

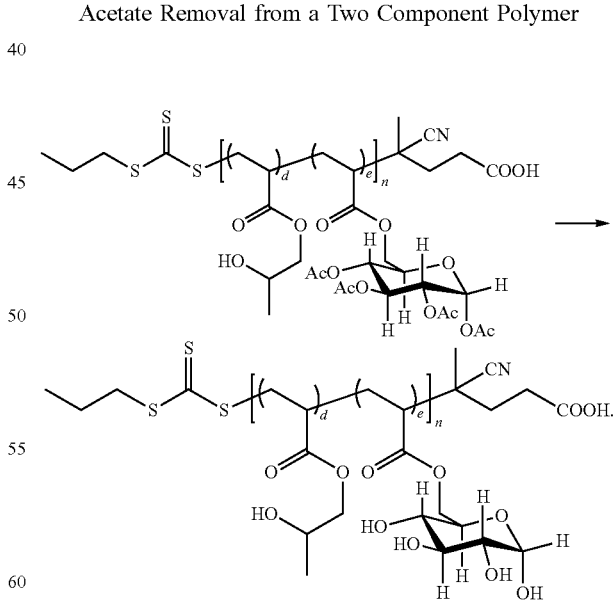

While the above reaction was successfully performed using NaOMe in CHCl$_3$/MeOH (1:1) at 22° C., the product had very limited solubility in THF, methanol, acetone and dichloromethane. Attempts to spray dry this deprotected polymer with probucol or phenytoin were unsuccessful.

Example 14

Acetate Removal From a Five Component Polymer

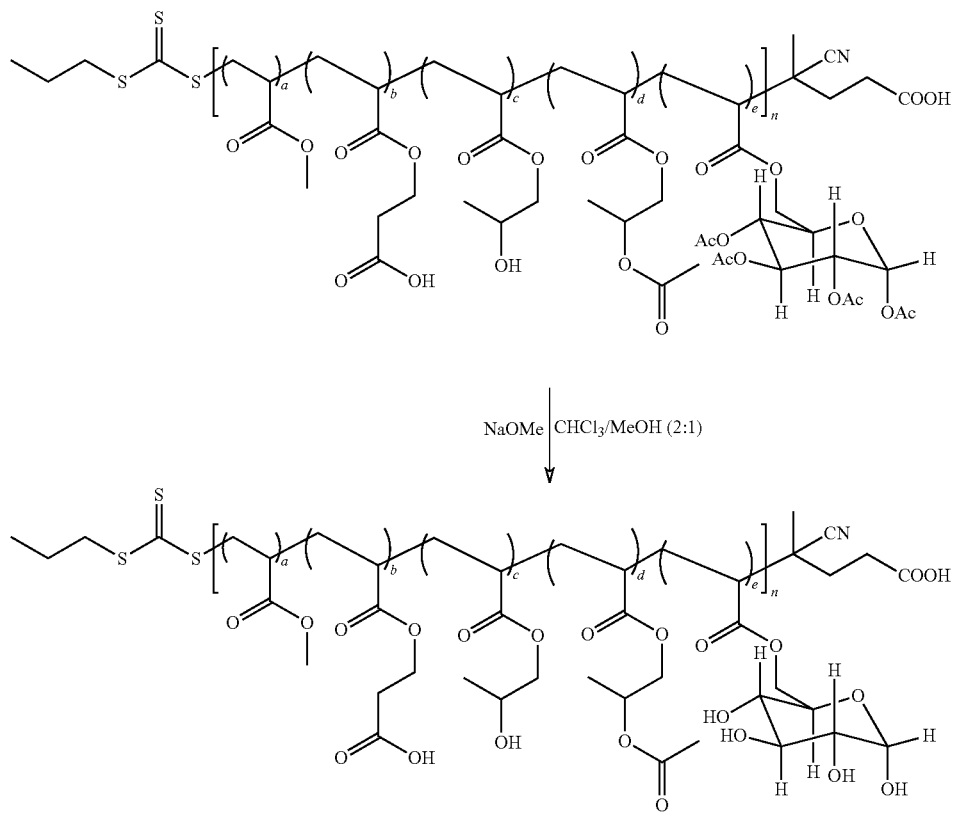

Figure 6:
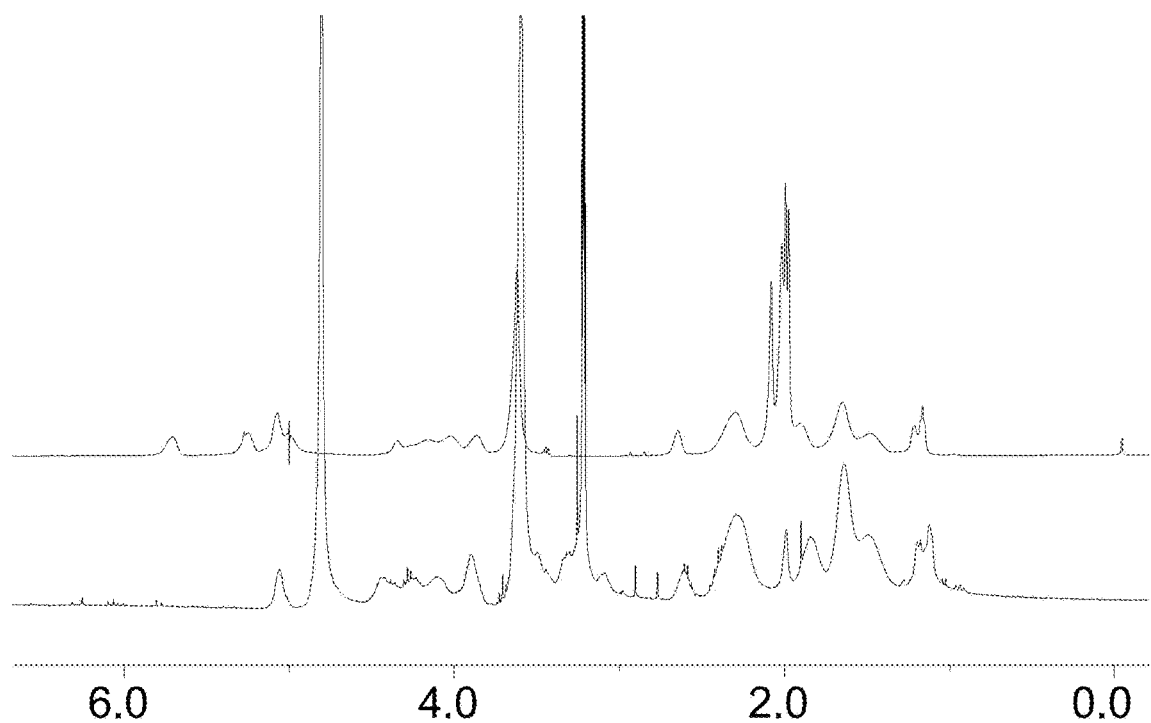
FIG. 6 shows a portion of two 300 MHz $^1$H NMR spectra. The top spectra is of an acetate protected, 5-component statistical copolymer (SCP) (which corresponds to Sample 1), while the bottom spectra is of the hydrolyzed (acetate groups removed) 5-component SCP.

The above reaction was successfully performed using NaOMe in CHCl$_3$/MeOH (1:1) at 22° C. The integrity of the trithiocarbonate end groups was maintained during the reaction. $^1$H NMR spectra of the starting material and product may be seen in FIG. 6, where the top spectrum is of the starting material, and clearly contains acetate groups (on the sugar moiety) at approximately 2 ppm, while the bottom spectrum is of the hydrolyzed product, and does not contain acetate groups (on the sugar moiety) at approximately 2 ppm.

Example 15

Optimal Polymer-Dissolution Relationships

Figure 7:
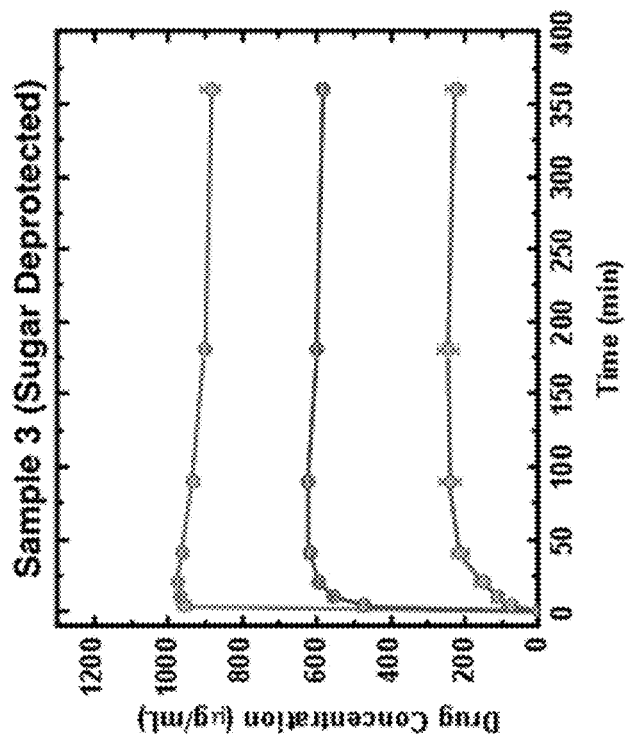
FIG. 7 shows a comparison of the concentration of probucol v. time when probucol is formulated with the SCP of Sample 3 in the protected (bottom graph) and deprotected form (top graph).
Figure 7:
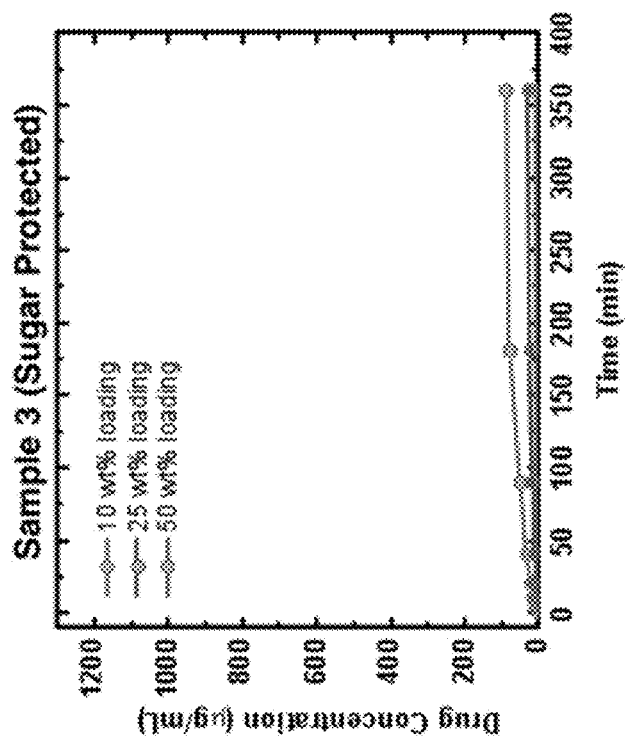

Selective acetate removal from five-component systems directly resulted in more hydrophilic polymers. This change in amphiphilicity led to distinct differences in dissolution performance of probucol, as seen in FIG. 7, where the dissolution profiles of the protected and deprotected Sample #3 (see Table 1) are shown, illustrating that the hydrophilic-hydrophobic balance of a polymer may be optimized to solubilize small drug molecules.

Example 16

Formulation Performance

Two different drugs, probucol and phenytoin, were formulated at different weight percent, using the polymers disclosed herein (see Table 1 for polymer sample numbers). The concentration-time area under the curve (AUC) from 0 to 360 min was determined using the trapezoidal rule. The AUC enhancement at 360 min is defined as a ratio of the spray-dried dispersion AUC to the crystalline drug AUC. For example, an AUC enhancement of 1 indicates no solubility enhancement over crystalline drug, while an AUC enhancement of 100 shows a 100-fold increase in the drug solubility. The results are illustrated in Table 16.

TABLE 16

| Polymer | Drug | Loading (wt %) | AUC$_{360\ min}$* Enhancement Factor |
|---|---|---|---|
| Sample 1 | probucol | 0.10 | 104000 |
| | | 0.25 | 91000 |
| | | 0.50 | 31000 |
| | phenytoin | 0.10 | 4.2 |
| | | 0.25 | 2.6 |
| | | 0.50 | 1.6 |
| Sample 2 | probucol | 0.10 | 38000 |
| | | 0.25 | 16000 |
| | | 0.50 | 5020 |
| | phenytoin | 0.10 | 1.3 |
| | | 0.25 | 1.2 |
| | | 0.50 | 1.1 |
| Sample 3 | probucol | 0.10 | 21000 |
| | | 0.25 | 7400 |
| | | 0.50 | 2800 |
| | phenytoin | 0.10 | 1.1 |
| | | 0.25 | 0.9 |
| | | 0.50 | 1.0 |
| Sample 4 | probucol | 0.10 | 6400 |
| | | 0.25 | 520 |
| | | 0.50 | 3300 |
| | phenytoin | 0.10 | 1.4 |

TABLE 16-continued

| Polymer | Drug | Loading (wt %) | AUC$_{360\,min}$* Enhancement Factor |
|---|---|---|---|
| | | 0.25 | 1.0 |
| | | 0.50 | 0.9 |
| Sample 5 | probucol | 0.10 | 320000 |
| | | 0.25 | 202000 |
| | | 0.50 | 47000 |
| | phenytoin | 0.10 | 1.6 |
| | | 0.25 | 1.3 |
| | | 0.50 | 1.1 |
| Sample 6 | probucol | 0.10 | 2200 |
| | | 0.25 | 1600 |
| | | 0.50 | 3400 |
| | phenytoin | 0.10 | 1.5 |
| | | 0.25 | 1.0 |
| | | 0.50 | 1.0 |
| Sample 8 | probucol | 0.10 | 17000 |
| | | 0.25 | 9200 |
| | | 0.50 | 2300 |
| | phenytoin | 0.10 | 1.6 |
| | | 0.25 | 1.3 |
| | | 0.50 | 1.1 |

*AUC$_{360\,min}$ is area under the curve (AUC) for 360 min period.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

What is claimed is:

1. A polymer having an acrylate-derived backbone, where the polymer is derived from at least a first monomer, a second monomer and a third monomer, wherein i) the first monomer is selected from the group consisting of a compound of formula (I), (II), and (III); ii) the second monomer is a compound of formula (IV) and iii) the third monomer is a compound of formula (V),

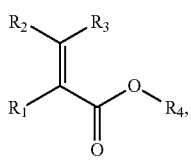
(I)

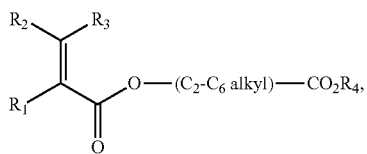
(II)

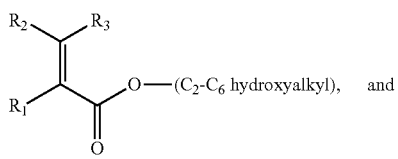
(III)

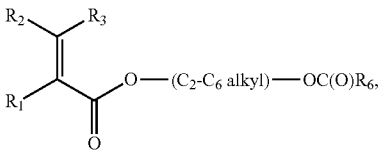
(IV)

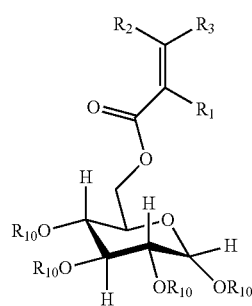
(V)

wherein at each occurrence, $R_1$, $R_2$ and $R_3$ are independently H or methyl;—

$R_4$ is H or C1-C$_6$ alkyl;

$R_6$ is C1-C$_6$ alkyl; and at each occurrence, $R_{10}$ is independently H, C1-C4 alkyl, C2-C4 alkanoyl, C2-C5 alkenoyl, —C1-C4 alkyl-aryl, or -alkanoylaryl;

wherein the C$_2$-C$_6$ hydroxyalkyl group has one or two OH groups.

2. A polymer according to claim 1, wherein at least one occurrence of $R_1$ is H.

3. A polymer according to claim 1, wherein at least one occurrence of $R_2$ is H.

4. A polymer according to claim 1, wherein at least one occurrence of $R_3$ is H.

5. A polymer according to claim 1, wherein $R_6$ is C1-C4 alkyl.

6. A polymer according to claim 1, wherein $R_{10}$ is —C(O)CH$_3$ or benzoyl.

7. A polymer according to claim 1, further comprising a fourth monomer selected from the group consisting of a compound of formula (I), (II), and (III), with the proviso that the first and fourth monomers are of different formulas.

8. A polymer according to claim 1, further comprising a fourth and fifth monomer, wherein the first monomer is a compound of formula (I), the fourth monomer is a compound of formula (II) and the fifth monomer is a compound of formula (III).

9. A polymer according to claim 1, wherein the compound of formula (I) has the formula:

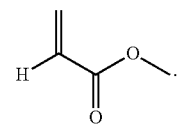

10. A polymer according to claim 1, wherein the compound of formula (II) has the formula:

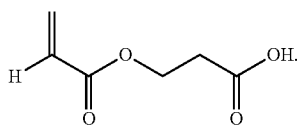

11. A polymer according to claim 1, wherein the compound of formula (III) has the formula:

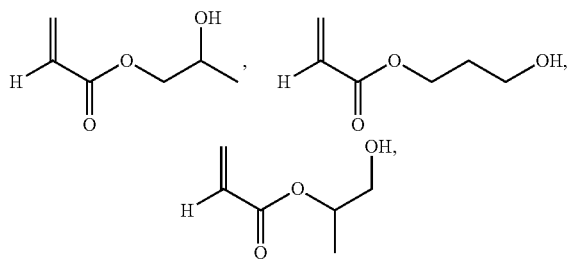

or combinations thereof.

12. A polymer according to claim 1, wherein the compound of formula (IV) has the formula:

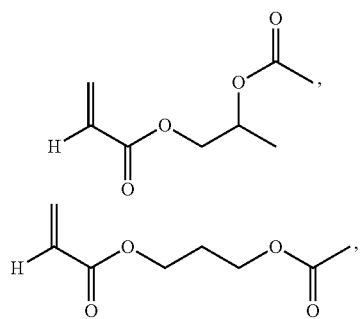

or combinations thereof.

13. A polymer according to claim 1, wherein the compound of formula (V) has the formula:

wherein each $R_{10}$ is —C(O)CH$_3$.

14. A polymer according to claim 1, wherein the polymer is a statistical polymer.

15. A method of making a polymer according to claim 1, comprising treating the monomers, with a free radical initiator in the presence of a chain transfer agent.

16. A pharmaceutical formulation comprising at least one polymer according to claim 1, and an active pharmaceutical ingredient.

17. A method of increasing the solubility of a drug, the method comprising formulating the drug at least one polymer according to claim 1.

18. A pharmaceutical formulation according to claim 16, wherein the formulation is in spray-dried form.

* * * * *